United States Patent

Siegel et al.

Patent Number: 5,182,371
Date of Patent: Jan. 26, 1993

[54] DOUBLED PHENYL- OR NAPHTHYL-AZOBENZENES HAVING A PLURALITY OF REACTIVE GROUPS AND INTERMEDIATES THEREOF

[75] Inventors: Bernd Siegel, Ludwigshafen; Manfred Patsch, Wachenheim, both of Fed. Rep. of Germany

[73] Assignee: BASF Aktiengesellschaft, Ludwigshafen, Fed. Rep. of Germany

[21] Appl. No.: 835,484

[22] Filed: Feb. 14, 1992

[30] Foreign Application Priority Data

Mar. 9, 1991 [DE] Fed. Rep. of Germany ....... 4107692

[51] Int. Cl.$^5$ .................... C09B 62/09; C09B 62/513; D06P 1/38
[52] U.S. Cl. .................... 534/612; 534/634; 534/635; 534/637; 558/30; 8/549; 560/251; 564/50
[58] Field of Search ................ 534/612, 634, 635, 637

[56] References Cited

U.S. PATENT DOCUMENTS

| | | | |
|---|---|---|---|
| 4,045,209 | 8/1977 | Hainaut et al. | 71/98 |
| 4,841,028 | 6/1989 | Aeschilmann et al. | 534/637 X |
| 5,091,516 | 2/1992 | Siegel et al. | 534/635 X |

FOREIGN PATENT DOCUMENTS

| | | |
|---|---|---|
| 437699 | 7/1991 | European Pat. Off. |
| 3313725 | 10/1984 | Fed. Rep. of Germany ...... 534/637 |

Primary Examiner—Floyd D. Higel
Assistant Examiner—Fiona T. Powers
Attorney, Agent, or Firm—Oblon, Spivak, McClelland, Maier & Neustadt

[57] ABSTRACT

The reactive dyes have the formula

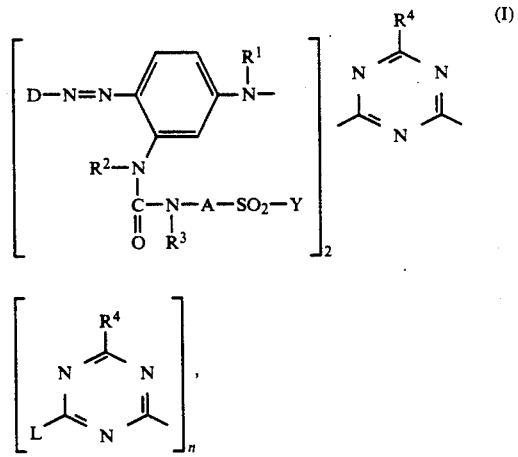

where
n is 0 or 1,
$R^1$, $R^2$ and $R^3$ are each hydrogen, $C_1$-$C_4$-alkyl or phenyl,
$R^4$ is fluorine, chlorine, bromine, $C_1$-$C_4$-alkylsulfonyl, phenylsulfonyl or a radical of the formula

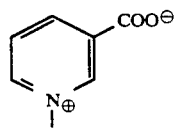

L is a bridgemember,
A is substituted or unsubstituted $C_2$-$C_8$-alkylene,
Y is vinyl or a radical of the formula —$CH_2$—$CH_2$—Q, where Q is a group which is detachable under alkaline reaction conditions, and
D is phenyl or naphthyl, which may each be substituted.

The present dyes are useful in dyeing or printing hydroxyl- or nitrogen-containing fibres.

3 Claims, No Drawings

DOUBLED PHENYL- OR NAPHTHYL-AZOBENZENES HAVING A PLURALITY OF REACTIVE GROUPS AND INTERMEDIATES THEREOF

The present invention relates to novel reactive dyes of the formula I

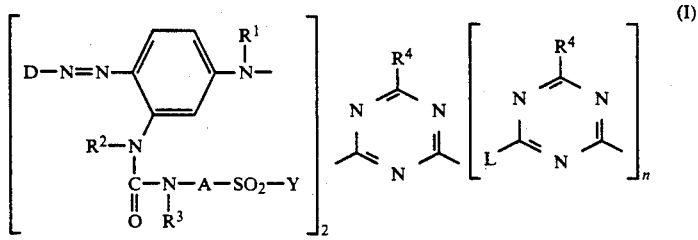

where
n is 0 or 1,
R$^1$, R$^2$ and R$^3$ are identical or different and each is independently of the others hydrogen, C$_1$-C$_4$-alkyl or phenyl,
R$^4$ is fluorine chlorine, bromine, C$_1$-C$_4$-alkylsulfonyl, phenylsulfonyl or a radical of the formula

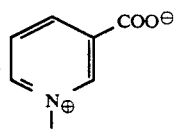

L is a bridge member,
A is C$_2$-C$_8$-alkylene which may be interrupted by from 1 to 3 oxygen atoms in ether function, imino groups or C$_1$-C$_4$-alkylimino groups,
Y is vinyl or a radical of the formula —CH$_2$—CH$_2$—Q, where Q is a group which is detachable under alkaline reaction conditions, and
D is phenyl or naphthyl, which may each be monosubstituted or polysubstituted by hydroxysulfonyl, carboxyl, C$_1$-C$_4$-alkoxycarbonyl, cyano, C$_1$-C$_4$-alkyl, C$_1$-C$_4$-alkoxy, halogen, nitro or vinylsulfonyl,
novel phenylenediamines as intermediates therefor and the use of the novel dyes for dyeing or printing hydroxyl- or nitrogen-containing fibers.

EP-A-174,909 discloses reactive dyes where the reactive group is a vinylsulfonyl radical which is bonded to the dye residue via a ureido group.

Furthermore, earlier European Patent Application EP-A- 437 699 describes similar dyes to those mentioned at the beginning, but they are not doubled.

It is an object of the present invention to provide novel reactive dyes which are doubled and have a vinylsulfonyl group which is bonded to the chromophore via a ureido group, which novel dyes shall have favorable application properties.

We have found that this object is achieved by the reactive dyes of the formula I defined at the beginning.

The novel reactive dyes of the formula I are in general represented in the present case in the form of the free acid. But their salts are of course also encompassed.

The salts which come into consideration here are in fact metal or ammonium salts. Metal salts are in particular the lithium, sodium or potassium salts. Ammonium salts for the purposes of the present invention are salts which contain either substituted or unsubstituted ammonium cations. Substituted ammonium cations are for example monoalkyl-, dialkyl-, trialkyl-, tetraalkyl- or benzyltrialkyl-ammonium cations or cations which are derived from nitrogen-containing five- or six-membered saturated heterocycles, such as pyrrolidinium, piperidinium, morpholinium, piperazinium or N-alkylpiperazinium cations or N-monoalkyl- or N,N-dialkyl-substituted products thereof. Alkyl here generally means straight-chain or branched C$_1$-C$_4$-alkyl which may be substituted by hydroxyl and/or interrupted by oxygen atoms.

Any substituted phenyl appearing in the above-mentioned formula I may, unless otherwise stated, have for example C$_1$-C$_4$-alkyl, C$_1$-C$_4$-haloalkyl, C$_1$-C$_4$-alkoxy, amino, C$_1$-C$_4$-mono- or -dialkylamino, nitro, formyl, cyano, carboxyl or hydroxysulfonyl as substituents. In general they have from 1 to 3 substituents.

R$^1$, R$^2$ and R$^3$ are each for example methyl, ethyl, propyl, isopropyl, butyl, isobutyl or sec-butyl.

R$^4$ is for example methylsulfonyl, ethylsulfonyl, propylsulfonyl, isopropylsulfonyl or butylsulfonyl.

A is for example —(CH$_2$)$_2$—, —(CH$_2$)$_3$—, —(CH$_2$)$_4$—, —(CH$_2$)$_5$—, —(CH$_2$)$_7$—, —(CH$_2$)$_8$—, —(CH$_3$)—$_2$—, —CH(CH$_3$)—CH(CH$_3$)—, —(CH$_2$)$_2$—O—(CH$_2$)$_2$—, —(CH$_2$)$_2$-NH-(CH$_2$)$_2$—, —(CH$_2$)$_2$-N(CH$_3$)—(CH$_2$)$_2$—, —(CH$_2$)$_2$—O—(CH$_2$)$_2$—O—(CH$_2$)$_2$— or —(CH$_2$)$_2$—O—(CH$_2$)$_2$—O—(CH$_2$)$_2$—.

Y in the formula I may inter alia be a group which is detachable under alkaline reaction conditions. Such groups are for example chlorine, OSO$_3$H, SSO$_3$H, OP(O)(OH)$_2$, C$_1$-C$_4$-alkylsulfonyloxy, substituted or unsubstituted phenylsulfonyloxy, C$_1$-C$_4$-alkanoyloxy, C$_1$-C$_4$-dialkylamino,

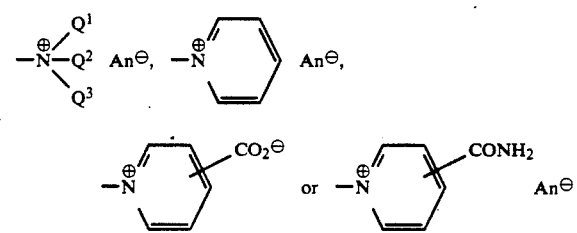

where Q$^1$, Q$^2$ and Q$^3$ are identical or different and each is independently of the others C$_1$-C$_4$-alkyl or benzyl, and Ar ⓡ is in each case an anion. (Suitable anions are for example fluoride, chloride, bromide, iodide, mono-, di- or trichloroacetate, methylsulfonate, phenylsulfonate or 2- or 4-methylphenylsulfonate.)

Suitable bridge members L conform for example to the formula

—NH—L¹—NH—,

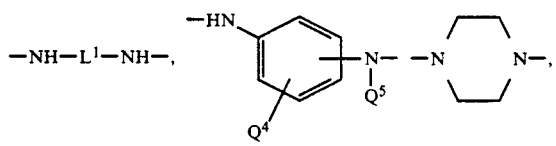

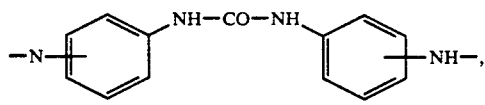

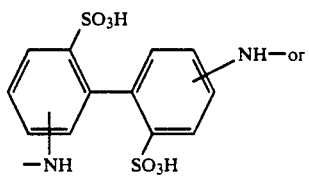

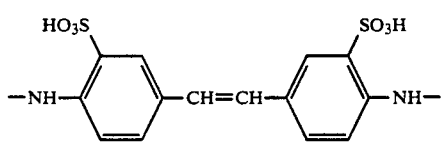

where L¹ is $C_2$-$C_8$-alkylene, $Q^4$ is hydrogen or hydroxysulfonyl, and $Q^5$ is hydrogen or $C_1$-$C_4$-alkyl.

Individual bridge members are for example radicals of the formula

—NH—$C_2H_4$—NH—, —NH—$C_3H_6$—NH—,

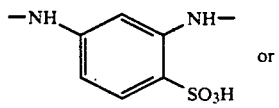

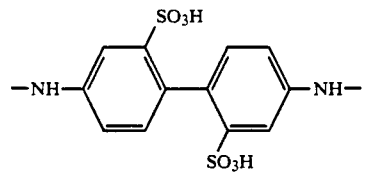

D is for example 2,4-dihydroxysulfonylphenyl, 2,5-dihydroxysulfonylphenyl, 2,5-dihydroxysulfonyl-4-methylphenyl, 2,5-dihydroxysulfonyl-6-chlorophenyl, 3,6,8-trihydroxysulfonylnaphth-2-yl, 4,6,8-trihydroxysulfonylnaphth-2-yl, 1,5-dihydroxysulfonylnaphth-2-yl or 1,6-dihydroxysulfonylnaphth-2-yl.

Preference is given to reactive dyes of the formula I where $R^1$, $R^2$ and $R^3$ are each hydrogen,
$R^4$ is fluorine or chlorine,
A is $C_2$-$C_4$-alkylene which may be interrupted by an oxygen atom in ether function, and
D is phenyl or naphthyl, which may each be monosubstituted, disubstituted or trisubstituted by hydroxysulfonyl.

Particular preference is given to reactive dyes of the formula I where

D is dihydroxysulfonylphenyl or trihydroxysulfonylnaphthyl.

Particular preference is further given to reactive dyes of the formula I where, when n is 1, L is a radical of the formula

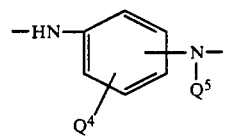

where $Q^4$ and $Q^5$ are each as defined above.

The novel reactive dyes of the formula I are obtained in an advantageous manner by conventionally diazotizing for example an amine of the formula III $$D-NH_2 \qquad (III)$$

where D is as defined above, and coupling it with a phenylenediamine of the formula II

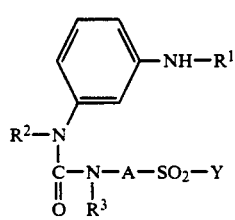 (II)

where $R^1$, $R^2$, $R^3$, A and Y are each as defined above.

The resulting azo dye of the formula IV

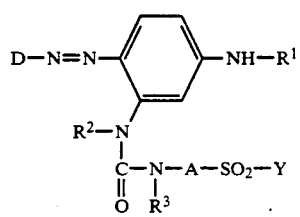 (IV)

where D, $R^1$, $R^2$, $R^3$, A and Y are each as defined above, can then be reacted with trihalotriazine in a conventional manner.

To obtain those dyes of the formula I where n is 0, the reaction product can be reacted with a further azo dye IV.

To obtain those dyes of the formula I where n is 1, the product formed in the reaction with trihalotriazine can then be reacted with a diamine of the formula V $$H_2N—L—NH_2 \qquad (V)$$

where L is as defined above.

The novel reactive dyes of the formula I are advantageous for dyeing or printing hydroxyl- or nitrogen-containing organic substrates. Such substrates are for example leather or fiber material which predominantly contains natural or synthetic polyamides or natural or regenerated cellulose. The novel dyes are preferred for dyeing and printing textile material based on cotton. The reactive dyes of the present invention can in some instances also be used for discharge printing.

The present invention further provides phenylenediamines of the formula II

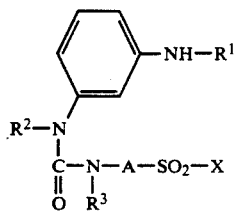

where
- $R^1$, $R^2$ and $R^3$ are identical or different and each is independently of the others hydrogen, $C_1$-$C_4$-alkyl or phenyl,
- A is $C_2$-$C_8$-alkylene which may be interrupted by from 1 to 3 oxygen atoms in ether function, imino groups or $C_1$-$C_4$-alkylimino groups, and
- X is vinyl, 2-acetoxyethyl or 2-sulfatoethyl.

As regards exemplification of the radicals mentioned, reference is made to the above remarks.

The novel phenylenediamines of the formula II can be obtained in a conventional manner, for example by reacting 3-nitrophenyl isocyanate of the formula VI

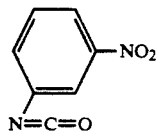

with a sulfur-containing amine of the formula VII

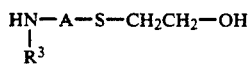

where $R^3$ and A are each as defined above, first oxidizing the thio group to a sulfone group in a conventional manner and then reducing the nitro group to an amino group in a conventional manner.

Conventional methods (e.g. esterification with acetic anhydride, acetyl chloride or sulfuric acid) can then also be employed to convert the hydroxy compound into the 2-acetoxyethyl or 2-sulfatoethyl compound, from which in turn the vinyl compound can be obtained in a conventional manner.

The phenylenediamine derivatives of the formula II of the present invention are useful intermediates for preparing the novel reactive dyes of the formula I.

The Examples which follow will further illustrate the invention. Preparation of intermediates The phenylenediamines used as coupling components in the Examples which follow can be prepared from the compounds described in Example 1 of earlier European Patent Application EP-A- 437 699 as follows:

EXAMPLE IM1

285 g (1 mol) of the compound of the formula

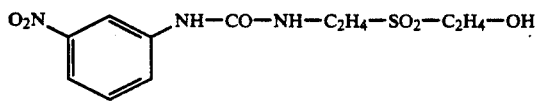

were heated to 95° C. together with 408 g (4 mol) of acetic anhydride. After the reaction had ended (check by TLC), the excess acylating agent was destroyed with water and the resulting precipitate was filtered off with suction at room temperature. This gave 323 g of a compound of the formula

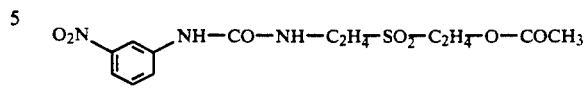

Melting point: 161–163° C.

The same method can be used to prepare the following derivatives:

Ex. No. IM2

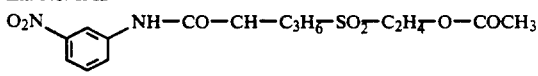

Ex. No. IM3

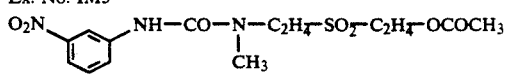

EXAMPLE IM4

359 g (1 mol) of the compound described in Example IM1 were suspended in 1000 ml of methanol and hydrogenated at 60° C. in the presence of Raney nickel. After the absorption of hydrogen had ceased, the catalyst was filtered off hot and the resulting precipitate was filtered off with suction at room temperature.

This gave 245 g of the compound of the formula

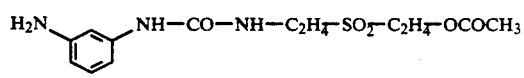

Melting point: 115–117° C.

The same method can be used to prepare the following derivatives:

Ex. No. IM5

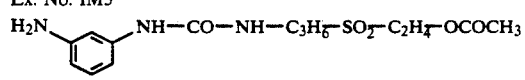

Ex. No. IM6

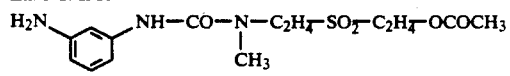

EXAMPLE IM7

285 g (1 mol) of the starting compound used in Example IM1 were introduced into 1000 g of chlorosulfonic acid and heated to 30–40° C. for about 2 hours. After the esterification had ended, the reaction mixture, which contained the sulfuric ester of the formula

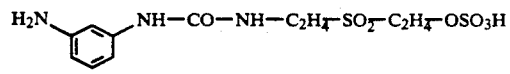

was decomposed with ice-water. The resulting solution was adjusted with 20% strength by weight sodium hydroxide solution to pH 10 and maintained at that pH until elimination was complete. The resulting precipitate was filtered off with suction, washed with water and dried. This left 190 g of the compound

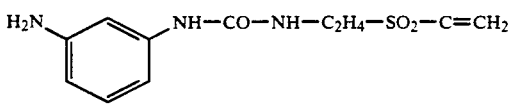

Melting point: 141–142° C.

The same method can be used to prepare the following derivatives:

Ex. No. IM8
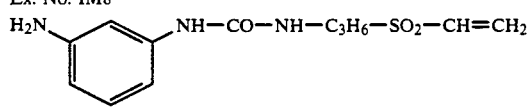

Ex. No. IM9
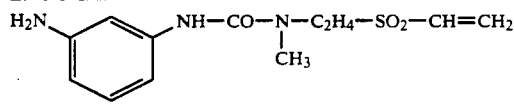

PREPARATION OF DYES

EXAMPLE 1 a) 101 g (0.4 mol) of aniline-2,4-disulfonic acid were diazotized in 400 ml of water acidified with hydrochloric acid and added to a suspension of 132 g (0.4 mol) of the product described in Example IM4 in 500 ml of water. The coupling reaction was carried out at 0–5° C. and pH 3 by adding 2N potassium bicarbonate solution.

b) The above-described reaction solution was halved, and the first half was condensed with 40.6 g (0.22 mol) of cyanuric chloride at 0–5° C. and pH 5.5. The solution was then clarified and reacted with the second half of the coupling solution at 40–50° C. and pH 5.5. The resulting reactive dye conforms to the formula

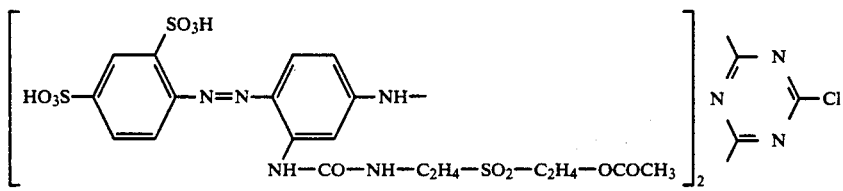

and was isolated by salting out. It dyes cotton in a yellow shade having a very good lightfastness and very good wetfastness properties.

c) 254 g (1 mol) of aniline-2,4-disulfonic acid were diazotized in 1000 g of an ice/water mixture at 0–5° C. with 320 ml of 23% strength by weight sodium nitrite solution. Then 330 g (1.0 mol) of the product described in Example IM4, suspended in 500 g of water, were added and the coupling reaction was carried out at a pH of 3 by means of 1 N sodium bicarbonate solution. The resulting coupling solution was then admixed with a mixture of 92 g of cyanuric chloride and 250 g of ice-water. Then the 1st condensation step was carried out at 0–5° C. and a pH of 5.5, set by adding sodium bicarbonate solution. After 1 hour the reaction mixture was heated to 40–45° C. for the 2nd condensation step and maintained at a pH of 5.5 by means of sodium bicarbonate solution. The resulting dye corresponds as free acid to the compound described in Example 1b and was isolated by spray drying.

The same method can be used to obtain the dyes of the formula

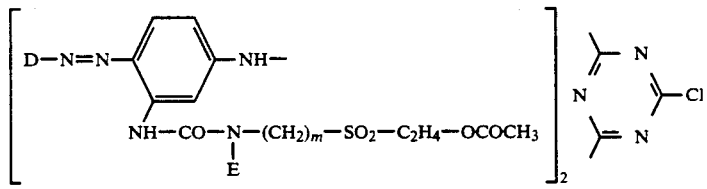

described in Table 1.

TABLE 1

| Ex. No. | D | E | m | Hue on Cotton |
|---|---|---|---|---|
| 2 | ![SO3H, HO3S benzene] | H | 2 | yellow |
| 3 | ![SO3H, O3S benzene] | H | 3 | yellow |
| 4 | ![SO3H, HO3S benzene] | CH3 | 2 | yellow |
| 5 | 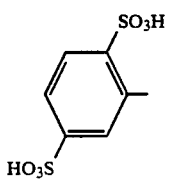 | H | 3 | yellow |

TABLE 1-continued

| Ex. No. | D | E | m | Hue on Cotton |
|---|---|---|---|---|
| 6 | 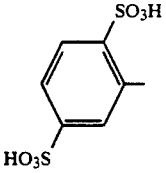 2,5-disulfo-4-methylphenyl (SO₃H, CH₃, HO₃S) | CH₃ | 2 | yellow |
| 7 | 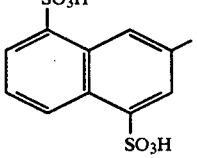 1,5-disulfo-7-methylnaphthyl | H | 2 | yellow |
| 8 | 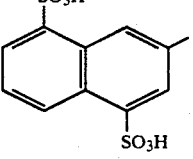 1,5-disulfo-7-methylnaphthyl | H | 3 | yellow |
| 9 | 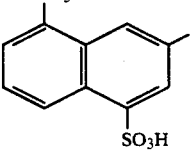 1,5-disulfo-7-methylnaphthyl | CH₃ | 2 | yellow |
| 10 | 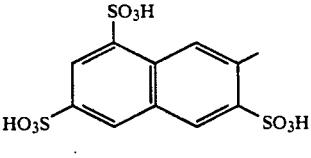 trisulfo-methylnaphthyl | H | 2 | reddish yellow |
| 11 | 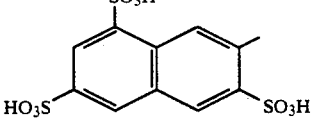 trisulfo-methylnaphthyl | H | 3 | reddish yellow |
| 12 | 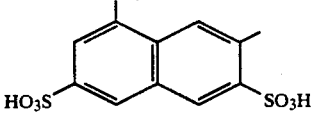 trisulfo-methylnaphthyl | CH₃ | 2 | reddish yellow |
| 13 | 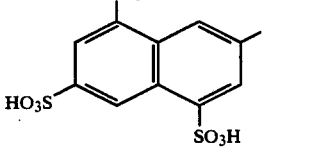 trisulfo-methylnaphthyl | CH₃ | 2 | reddish yellow |
| 14 | 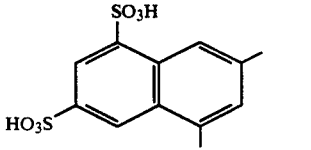 trisulfo-methylnaphthyl | H | 3 | reddish yellow |
| 15 | 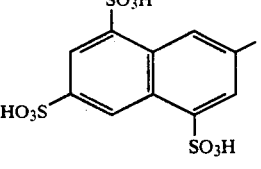 trisulfo-methylnaphthyl | CH₃ | 2 | reddish yellow |
| 16 | 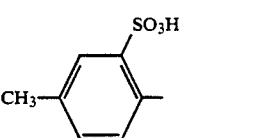 2,4-disulfo-5-methylphenyl | H | 2 | yellow |
| 17 | 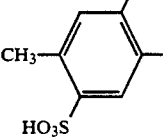 2,4-disulfo-5-methylphenyl | H | 3 | yellow |
| 18 | 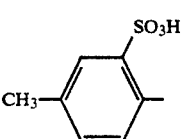 2,4-disulfo-5-methylphenyl | CH₃ | 2 | yellow |
| 19 | 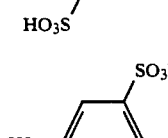 4-chloro-2,5-disulfophenyl | H | 2 | yellow |
| 20 | 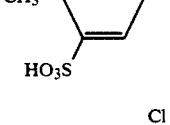 4-chloro-2,5-disulfophenyl | H | 3 | yellow |
| 21 | 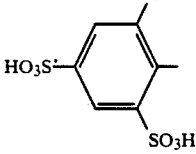 4-chloro-2,5-disulfophenyl | CH₃ | 2 | yellow |

EXAMPLE 22

101 g (0.4 mol) of aniline-2,4-disulfonic acid were diazotized in 400 ml of water acidified with hydrochloric acid and added to a suspension of 107.6 g (0.4 mol) of the product described in Example IM7 in ml of water. The coupling reaction was carried out at 0-5° C. by adding 2N potassium bicarbonate solution. The reaction solution was then halved, the first half admixed with 40.6 g (0.22 mol) of cyanuric chloride, and pH 5.5 was maintained at 0-5° C. by means of 2N potassium bicarbonate solution until condensation was complete. The reaction solution was clarified and reacted with the second half of the coupling solution at 40–50° C. and pH 5.5. The resulting dye was isolated by evaporating the reaction solution to dryness. It conforms to the formula

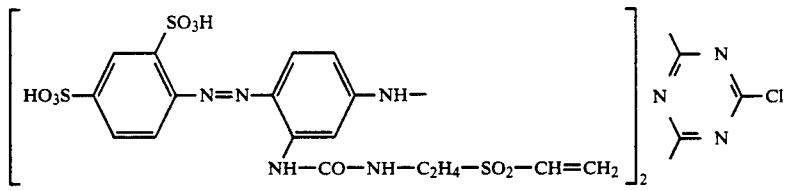

and dyes cotton in a yellow shade.

The same method can be used to obtain the dyes of the formula

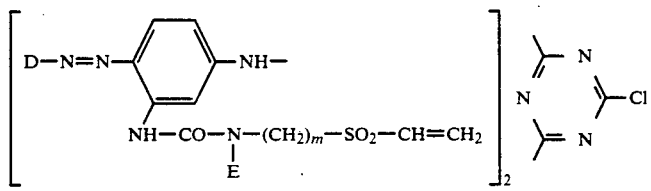

listed in Table 2.

TABLE 2

| Ex. No. | D | E | m | Hue on cotton |
|---|---|---|---|---|
| 23 | 2,5-disulfophenyl (SO₃H top, HO₃S bottom) | H | 2 | yellow |
| 24 | 2,5-disulfophenyl | H | 3 | yellow |
| 25 | 2,5-disulfophenyl | CH₃ | 2 | yellow |
| 26 | 2,4-disulfophenyl | H | 3 | yellow |
| 27 | 2,4-disulfophenyl | CH₃ | 2 | yellow |
| 28 | 1,5-disulfo-7-methylnaphthyl | H | 2 | yellow |
| 29 | 1,5-disulfo-7-methylnaphthyl | H | 3 | yellow |
| 30 | 1,5-disulfo-7-methylnaphthyl | CH₃ | 2 | yellow |
| 31 | 1,6-disulfo-7-methylnaphthyl | H | 2 | reddish yellow |
| 32 | 1,6-disulfo-7-methylnaphthyl | H | 3 | reddish yellow |
| 33 | 1,6-disulfo-7-methylnaphthyl | CH₃ | 2 | reddish yellow |

TABLE 2-continued

| Ex. No. | D | E | m | Hue on cotton |
|---|---|---|---|---|
| 34 | naphthalene with SO₃H, HO₃S, SO₃H | H | 2 | reddish yellow |
| 35 | naphthalene with SO₃H, HO₃S, SO₃H | H | 3 | reddish yellow |
| 36 | naphthalene with SO₃H, HO₃S, SO₃H | CH₃ | 2 | reddish yellow |
| 37 | benzene with SO₃H, CH₃, SO₃H | H | 2 | yellow |
| 38 | benzene with SO₃H, CH₃, SO₃H | H | 3 | yellow |
| 39 | benzene with SO₃H, CH₃, HO₃S | CH₃ | 2 | yellow |
| 40 | benzene with Cl, HO₃S, SO₃H | H | 2 | yellow |
| 41 | benzene with Cl, HO₃S, SO₃H | H | 3 | yellow |
| 42 | benzene with Cl, HO₃S, SO₃H | CH₃ | 2 | yellow |

EXAMPLE 43

101 g (0.4 mol) of aniline-2,4-disulfonic acid were diazotized in 400 ml of water acidified with hydrochloric acid and added to a solution of 146.8 g (0.4 mol) of the sulfuric ester described in Example IM7 in 500 ml of water. The coupling reaction was carried out at 0–5° C. by adding 2N sodium hydroxide solution. The coupling solution was then halved, the first half admixed with 40.6 g (0.22 mol) of cyanuric chloride, and pH 5.5 was maintained at 0–5° C. by means of 2N sodium hydroxide solution until condensation was complete. The reaction solution was clarified and reacted with the second half of the coupling solution at 40–50° C. and pH 5.5. The resulting dye was isolated by salting out. It conforms to the formula

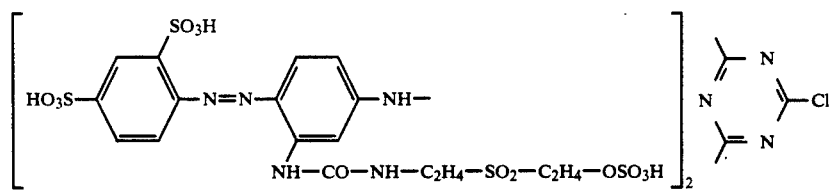

and dyes cotton in a yellow shade.

The same method can be used to obtain the dyes of the formula

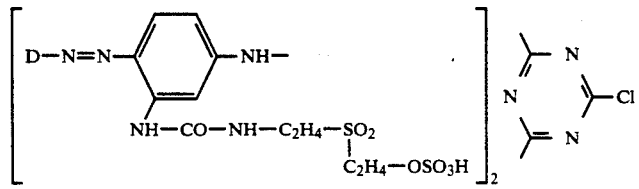

listed in Table 3.

TABLE 3

| Example No. | D | Hue on cotton |
|---|---|---|
| 44 | 2-methylbenzene-1,4-disulfonic acid (SO3H top, HO3S bottom, CH3) | yellow |
| 45 | 7-methylnaphthalene-1,5-disulfonic acid | yellow |
| 46 | 7-methylnaphthalene-1,3,6-trisulfonic acid | yellow |
| 47 | 7-methylnaphthalene-1,3,5-trisulfonic acid | yellow |

TABLE 3-continued

| Example No. | D | Hue on cotton |
|---|---|---|
| 48 | 4-methylbenzene with SO3H, HO3S, H3C | yellow |
| 49 | 3-chlorobenzene with SO3H, HO3S, Cl | yellow |

EXAMPLE 50

0.4 mol of the coupling solution described in Example 1 was condensed with 81.2 g (0.44 mol) of cyanuric chloride at 1–15° C. and pH 5.5. The reaction solution was then clarified and admixed with 21.6 g (0.2 mol) of para-phenylenediamine. To complete the reaction the reaction mixture was heated to 40–50° C. and a pH of 5.5 was maintained by adding 2N sodium hydroxide solution. The dye was isolated by spray drying and conforms to the formula

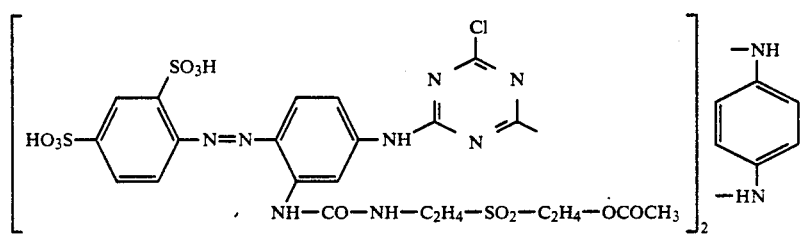

It dyes cotton in a yellow shade.

The same method can be used to obtain the dyes of the formula

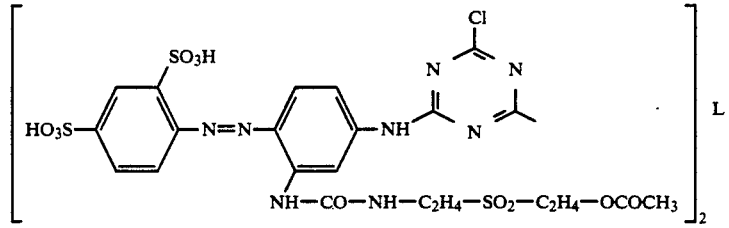

listed in Table 4.

TABLE 4

| Example No. | L | Hue on cotton |
|---|---|---|
| 51 | —HN—(1,3-phenylene)—NH— | yellow |
| 52 | —HN—C2H4—NH— | yellow |
| 53 | —HN—C3H6—NH— | yellow |

TABLE 4-continued

| Example No. | L | Hue on cotton |
|---|---|---|
| 54 | —N⌒N— (piperazine) | yellow |
| 55 | —HN—C6H4—NHCNH—C6H4—NH— (with C=O bridge, 3,3'-linked) | yellow |

EXAMPLE 56

0.4 mol of the coupling solution described in Example 1 was reacted with 81.2 g (0.44 mol) of cyanuric chloride at 0–5° C. and pH 5.5. The reaction solution was then clarified and admixed with 37.6 g (0.2 mol) of 2,4-diaminobenzenesulfonic acid. To complete the reaction, the reaction mixture was heated to 40–50° C.) and a pH of 5.5 was maintained with 2N sodium hydroxide solution. The resulting dye was isolated by evaporating the reaction solution to dryness. It conforms to the formula

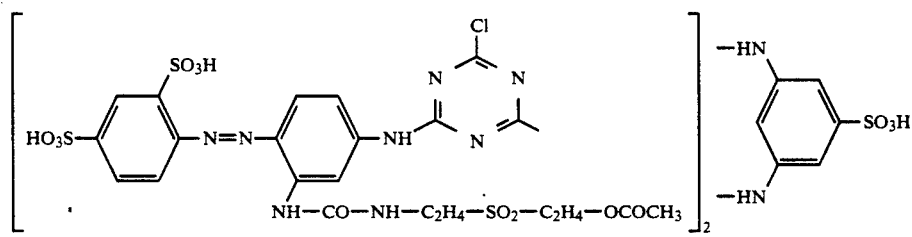

and dyes cotton in a yellow shade.

The same method can be used to obtain the dyes of the formula

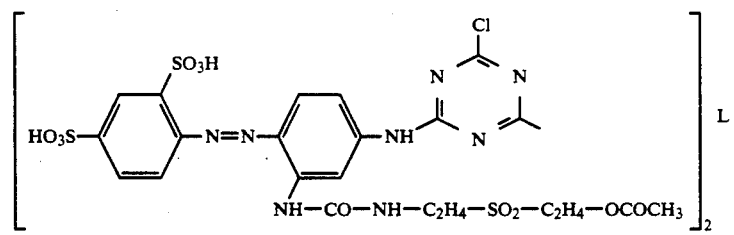

listed in Table 5.

TABLE 5

| Example No. | L | Hue on cotton |
|---|---|---|
| 57 | —HN—C6H3(SO3H)—NH— (2,4-diamino, SO3H at 1) | yellow |
| 58 | —HN—C6H3(SO3H)—NH— (isomer) | yellow |
| 59 | —HN—C6H3(CH3)(SO3H)—N— | yellow |
| 60 | —HN—C6H3(SO3H)—C6H3(SO3H)—NH— (biphenyl, 2,2'-disulfo) | yellow |
| 61 | —HN—C6H3(SO3H)—CH=CH—C6H3(SO3H)—NH— | yellow |

We claim:
1. A reactive dye of the formula I

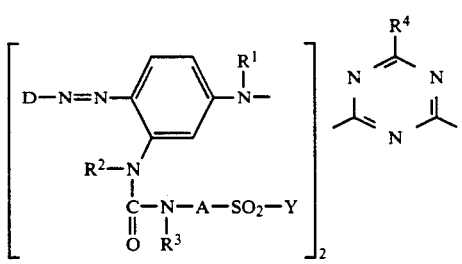 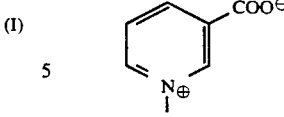 (I)

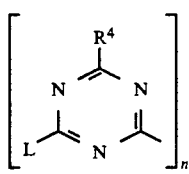

where n is 0 or 1, $R^1$, $R^2$ and $R^3$ are identical or different and each is independently of the others hydrogen, $C_1$-$C_4$-alkyl or phenyl $R^4$ is fluorine, chlorine, bromine, $C_1$-$C_4$-alkylsulfonyl, phenylsulfonyl or a radical of the formula L is a bridge member, A is $C_2$-$C_8$-alkylene which may be interrupted by from 1 to 3 oxygen atoms in ether function, imino groups or $C_1$-$C_4$-alkylimino groups, Y is vinyl or a radical of the formula —$CH_2$—$CH_2$—Q, where Q is a group which is detachable under alkaline reaction conditions, and D is phenyl or naphthyl, which may each be monosubstituted or polysubstituted by hydroxysulfonyl, carboxyl, $C_1$-$C_4$-alkoxycarbonyl, cyano, $C_1$-$C_4$-alkyl, $C_1$-$C_4$-alkoxy, halogen, nitro or vinylsulfonyl.

2. A reactive dye as claimed in claim 1, wherein $R^1$, $R^2$ and $R^3$ are each hydrogen, $R^4$ is fluorine or chlorine, A is $C_2$-$C_4$-alkylene which may be interrupted by an oxygen atom in ether function, and D is phenyl or naphthyl, which may each be monosubstituted, disubstituted or trisubstituted by hydroxysulfonyl.

3. A method of using a reactive dye as claimed in claim 1 for dyeing or printing hydroxyl-ornitorgen-containing organic substrates.

* * * * *